United States Patent [19]
Tsirjulnikov et al.

[11] Patent Number: 4,872,447
[45] Date of Patent: Oct. 10, 1989

[54] METHOD FOR TREATMENT OF SEXUAL IMPOTENCE IN MEN

[75] Inventors: Moisei V. Tsirjulnikov; Zinovy A. Zusmanovsky, both of Leningrad, U.S.S.R.

[73] Assignee: Vseojunzy Nauchno-Issledovatelsky 1 Ispytatelny Institut Meditsinskoi Tekhniki

[21] Appl. No.: 166,678
[22] Filed: Mar. 11, 1988
[51] Int. Cl.⁴ .............................................. A61F 5/41
[52] U.S. Cl. ..................................................... 128/79
[58] Field of Search ......................................... 128/79

[56] References Cited

U.S. PATENT DOCUMENTS 4,362,152 12/1982 Gorokhovsky et al. ............. 128/79
4,488,541 12/1984 Garcia .................................. 128/79
4,640,270 2/1987 Chin .................................... 128/79

FOREIGN PATENT DOCUMENTS 589978 1/1978 U.S.S.R. ................................ 128/79

Primary Examiner—Gene Mancene
Assistant Examiner—Cary E. Stone
Attorney, Agent, or Firm—Burgess, Ryan and Wayne

[57] ABSTRACT

A method for treatment of sexual impotence in men incorporates an external fixing of the penis with the aid of mechanical device, followed by rehabilitation of the sexual potence. According to the invention, rehabilitation is carried out by successive releasing of the penis from fixing through stage-by-stage displacement of the fixing points towards the root of the penis so as to increase the length of penis portion released from fixing and accompanied by regulation of the regional blood flow through the penis by virtue of a mechanical action exerted on the penis at the fixing points.

2 Claims, 1 Drawing Sheet

METHOD FOR TREATMENT OF SEXUAL IMPOTENCE IN MEN

FIELD OF THE INVENTION

The present invention relates generally to medicine and has particular reference to method for treatment of sexual impotence in men.

The invention is applicable for treatment of sexual impotence in men which is largely of a functional (psychogenic) or functional-organic origin.

BACKGROUND ART

There are extensively known some methods for treatment of sexual impotence in men which make provision for a complex of measures of a psychotherapeutic, medicamentous, physiotherapeutic, health resort, or other nature.

However, the heretofore-known methods of treatment are too prolonged, expensive and require an individual approach to a patient, and what is more are far from being always efficacious.

It is a method for treatment of sexual impotence in men (SU, A, 589,978) that makes it possible to cut down the duration and increase the efficiency of treatment of sexual impotence in men, said method including an external fixing of the penis through mechanical means, which are then dispensed with as soon as a positive effect is attained, i.e., in cases where an adequate degree of true erection ensues and retains stably in the course of repeated coitus.

It is not infrequently however that rehabilitation of the male potency (potentia coeundi) is necessary, especially in psychogenic forms of sexual impotence, since relapses of the disease may occur due to patient's fear for a successful performance of a sexual intercourse, which necessitates a further treatment course.

The methods of rehabilitation of sexual ability in men that have been applied up to now incorporate prolonged complex psychotherapeutic, health-resort, and other measures.

SUMMARY OF THE INVENTION

It is an object of the invention to provide a method for treatment of sexual impotence in men, wherein rehabilitation of the male potency makes it possible to cut down the treatment course.

It is another object of the invention to render relapses of the disease less probable.

It is one more object of the invention that follows from the preceding ones, to provide higher efficacy of treatment.

Said objects are accomplished due to the provision of the herein-proposed method for treatment of sexual impotence in men, including an external fixation of the penis with the aid of mechanical means followed by rehabilitation of the sexual potency, wherein, according to the invention, rehabilitation is carried out by successively releasing the penis from fixation by virtue of a stage-by-stage displacement of the fixing points towards the root of the penis, so as to increase the length of the penis portion free from fixation, accompanied by regulation of the regional blood flow through the penis by way of mechanical action exerted thereon at the points of fixation.

It is expedient that fixation of the penis and regulation of the regional blood flow therein be carried out at the first stage in the proximal, middle and distal portions of the penis, at the second stage, in the proximal and middle portions, and at the third stage, in the proximal portion of the penis.

The aforesaid stage-by-stage rehabilitation makes it possible to considerably cut down the course of treatment of sexual impotence in men, provide for high efficiency of the treatment and prevent a possibility of relapses upon termination of the treatment, especially in cases of psychogenic (functional) and functional-organic forms of the disease.

BRIEF DESCRIPTION OF THE DRAWINGS

The essence and further advantageous features of the invention will become apparent from a consideration of the hereinbelow-stated description with reference to the accompanying drawings, wherein.

DETAILED DESCRIPTION OF THE INVENTION

Figure 1:
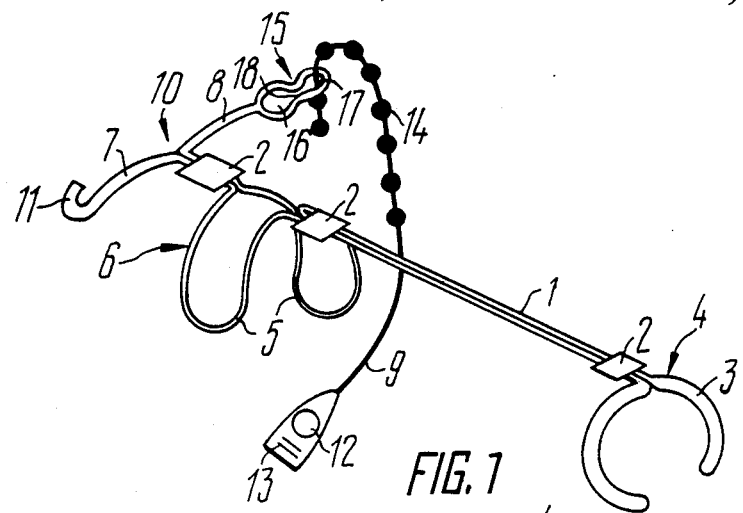
FIG. 1 is a general schematic view of a device for carrying into effect the method for treatment of sexual impotence in men, according to the invention.

The herein-proposed method of treatment is carried out with the aid of the device which provides for an external fixing of the penis, said device comprising, (FIG. 1), e.g., two parallel rods 1 made of metal wire and mounted in sleeves 2 rotatably about their geometric axes. Each of the rods 1 is connected, at one of its ends, to the end of an arc-shaped element 3 made as a plate curved to follow the shape of the coronary sulcus of the penis. Both of the arc-shaped elements 3 form a retainer 4 of the glans penis. The rods 1 are connected, in their middle portion, to arc-shaped elements 5 curved into a loop whose semiarcs encompass the penis circumferentially to form a control retainer 6. At the opposite end the rods are connected to the ends of arc-shaped elements 7 and 8 which form together with an elastic element 9 made of rubber, a retainer for the root of the penis. The vacant end of the arc-shaped element 7 is provided with a hook 11 which is adapted to interact with the hole of the eyelet 12 provided at one of the ends of the elastic element 9. The eyelet 12 is made integral with the elastic element 9 and has a holder 13. Spherical bulges 14 are provided at the opposite end of the elastic element 9, said bulges being adapted to interact with a lock 15 disposed at the free end of the arc-shaped element 8. The lock 15 is in fact two holes 16 and 17 interconnected through a recess 18. The diameter of the hole 16 exceeds the diameter of the spherical bulge 14 on the elastic element 9, whereas the diameter of the hole 17 is smaller than that of the spherical bulge. The surface of the metallic elements 1, 2, 3, 5, 7, and 8 have an elastic coating.

The device is fitted onto a relaxed penis so that the retainer 4 of the glans penis should encompass the coronary sulcus of the penis, the control retainer 6, the middle portion of the penis, and the retainer 10 of the root of the penis should encompass the radix penis behind the scrotum at the pubic bone with its arc-shaped elements 7, 8 and the elastic element 9. As a result, the eyelet 12 of the elastic element 9 is fitted, by the holder 13, onto the hook 11 of the arc-shaped element 7. The degree of tension of the elastic element 9 is adjusted by selecting the proper spherical bulge 14 inserted into the lock 15. The spherical bulge 14 is fixed in position in the lock 15 as follows: the end of the elastic element 9 is inserted into the larger-diameter hole 16 at the level of the preselected spherical bulge 14 and is moved along the recess 18 into the smaller-diameter hole 17, which holds the spherical bulge 14 in place. Should the length of the elastic element deciding the degree of its tension be selected not properly, the elastic element 9 is withdrawn in a reverse order and shortened or lengthened due to selection of another properly fitted spherical bulge 14 and holding it in the hole 17.

Thus, the penis acquires the position which enables one to perform a sexual intercourse without any sensation of discomfort for both partners.

The proposed method is carried out as follows.

Figure 2:
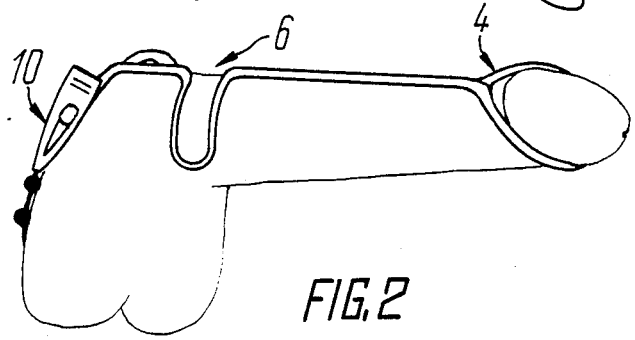
FIG. 2 illustrates fixation of the penis in the proximal, middle and distal portions thereof with the aid of the device shown in FIG. 1.

The penis of the male partner in a relaxed state is fixed throughout its length at its distal, middle, and proximal portions with the use of a mechanical means, such as, e.g., the hereinabove-described device, by placing the retainers 4, 6, 10 along the coronary sulcus of the penis in the middle portion and at the root of the penis, respectively (FIG. 2). Transient restriction of the coronary blood flow occurs in the penis due to a pressure exerted by the retainers 4, 6, 10, specifically in its distal, middle, and proximal portions, which promotes the erection of the penis and enables one to perform a sexual intercourse irrespective of the degree of erection thus occurred and to continue the friction stage of a sexual act for as long period of time as necessary.

When performing a sexual intercourse with the help of a mechanical means the patient gets released from psychogenic causes of inhibition of the sexual function, while new viscero-cortical conditioned-reflex connections arise due to the action on the reflexogenic zone of the penis.

Upon setting-in of a true erection the distal portion of the penis is released with a view to preclude relapses of the disease and to continue rehabilitation, while the middle portion of the penis remains fixed as far as the radix penis, thus replacing the full restriction of the regional venous blood flow by a partial one. This is attained due to the provision of some additional contrivances in the outfit of the device which follow the construction of the main device but each of them is shorter and has by one retainer less than the preceding one, starting from the retainer 4 of the glans penis.

Figure 3:
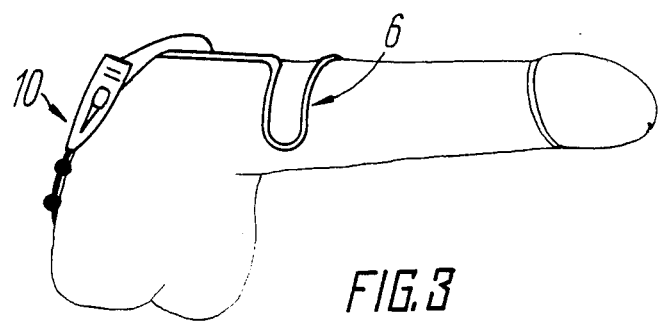
FIG. 3 illustrates fixation of the penis in the proximal and middle portions thereof with the aid of the shortened device devoid of the retainer of the glans penis and some of the interconnecting rods.

FIG. 3 presents the device for fixing the proximal and middle portions of the penis, devoid of the glans penis retainer and some of the rods 1.

For some period of time the patient keeps performing sexual intercourses with the distal portion of the penis released from fixing, thus becoming accustomed to the fact that he is able to perform normal sexual acts with the glans penis not fixed, which in turn encourages the fixing of the conditioned-reflex connections and eliminates the psychogenic mechanisms inhibiting the sexual function.

Figure 4:
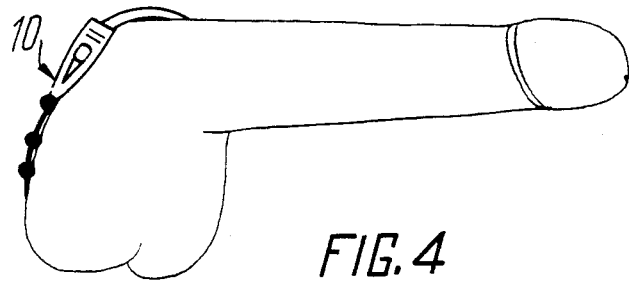
FIG. 4 illustrates fixation of the penis in the proximal portion thereof with the aid of the still more shortened device devoid of the retainer of the glans penis, the control retainer and interconnecting rods showing said device mounted on the root of penis.

Upon further fortification of the degree of true erection at the next stage of treatment the middle portion of the penis is released from fixation, thus maintaining it only at the radix penis (FIG. 4), which restricts the regional venous blood flow in the proximal portion alone, by making use of the still more shortened device devoid of the glans penis retainer, the rods, and the control retainer.

Once the patient has become absolutely sure that his sexual function is restored completely, the retainer 10 of the radix penis is removed and the patient gets fully able to perform normal sexual intercourses without the use of any mechanical aids.

Treatment of sexual impotence in men by means of the method incorporating a stage-by-stage rehabilitation of sexual potency, according to the invention, fosters the attainment of a rapid and stable curative effect.

What is claimed is:

1. A method for treatment of sexual impotence in men, comprising an external fixing of the penis with the aid of mechanical means followed by rehabilitation of the sexual potency which is carried out by a stage-by-stage displacement of the points of fixing towards the root of the penis, thus increasing the length of the penis portion free from fixing and accompanied by regulation of the regional blood flow through the penis by way of mechanical action exerted thereon at the points of fixing.

2. A method for treatment of sexual impotence in men, comprising an external fixing of the penis with the aid of mechanical means followed by rehabilitation of the sexual potency which is carried out by a stage-by-stage displacement of the points of fixing towards the root of the penis, wherein fixing of the penis and regulation of the regional blood flow therein are carried out at a first stage in the proximal, middle, and distal portions of the penis, at a second stage, in the proximal and middle portions, and at a third stage, in the proximal portion of the penis, thus increasing the length of the penis portion free from fixing and accompanied by regulation of the regional blood flow through the penis by way of mechanical action exerted thereon at the points of fixing.

* * * * *